(12) United States Patent
Hua et al.

(10) Patent No.: US 10,481,386 B2
(45) Date of Patent: Nov. 19, 2019

(54) OPTICAL ARTICLE AND ILLUMINATION SYSTEM FOR ENDOSCOPE

(71) Applicant: ARIZONA BOARD OF REGENTS ON BEHALF OF THE UNIVERSITY OF ARIZONA, Tucson, AZ (US)

(72) Inventors: Hong Hua, Tucson, AZ (US); Rengmao Wu, Tucson, AZ (US); Yi Qin, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 353 days.

(21) Appl. No.: 15/471,994

(22) Filed: Mar. 28, 2017

(65) Prior Publication Data

US 2017/0285324 A1  Oct. 5, 2017

Related U.S. Application Data

(60) Provisional application No. 62/315,423, filed on Mar. 30, 2016.

(51) Int. Cl.
| | |
|---|---|
| *G02B 23/24* | (2006.01) |
| *F21V 8/00* | (2006.01) |
| *G02B 3/02* | (2006.01) |
| *A61B 1/07* | (2006.01) |
| *A61B 1/313* | (2006.01) |
| *A61B 1/00* | (2006.01) |
| *A61B 1/06* | (2006.01) |

(52) U.S. Cl.
CPC ...... *G02B 23/2469* (2013.01); *A61B 1/00096* (2013.01); *A61B 1/00165* (2013.01); *A61B 1/0607* (2013.01); *A61B 1/07* (2013.01); *A61B 1/3132* (2013.01); *G02B 3/02* (2013.01); *G02B 6/0008* (2013.01)

(58) Field of Classification Search
None
See application file for complete search history.

(56) References Cited

U.S. PATENT DOCUMENTS

| | | | | |
|---|---|---|---|---|
| 5,630,784 | A * | 5/1997 | Siegmund | A61B 1/042 385/133 |
| 7,236,665 | B2 * | 6/2007 | Kobayashi | G02B 6/32 385/119 |
| 2004/0143167 | A1 * | 7/2004 | Branch | A61B 17/0218 600/212 |

(Continued)

*Primary Examiner* — Chad H Smith
(74) *Attorney, Agent, or Firm* — Quales & Brady LLP; Yakov S. Sidorin

(57) ABSTRACT

An optical element, wherein axially symmetric or not, an output surface of which contains a plurality of indentations configured to increase a degree of divergence of light that is incident onto such surface through an input surface of the optical element. In one implementation, each of the indentations defines a corresponding aspheric lenslet the plurality of which encircles the central opening in the optical element. The optical element can he configured as a lightguide having the specified output surface. An illumination system for a laparoscope employing such optical element as an addition to the optical fiber bundle of the laparoscope or as a fiber bundle itself that has the specified output surface.

13 Claims, 16 Drawing Sheets

(56) References Cited

U.S. PATENT DOCUMENTS

| | | | | |
|---|---|---|---|---|
| 2010/0080016 A1* | 4/2010 | Fukui | ................... | A61B 1/0653 |
| | | | | 362/574 |
| 2011/0201889 A1* | 8/2011 | Vayser | ............... | A61B 1/00135 |
| | | | | 600/182 |
| 2016/0022119 A1* | 1/2016 | Shahmoon | ......... | A61B 1/00096 |
| | | | | 600/182 |

* cited by examiner

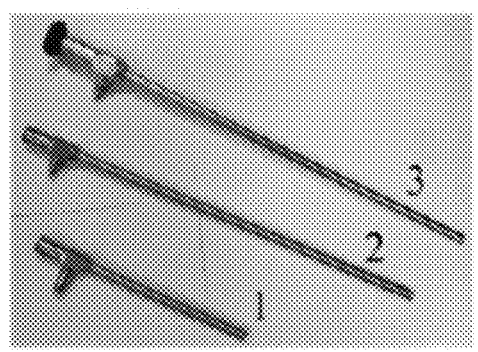
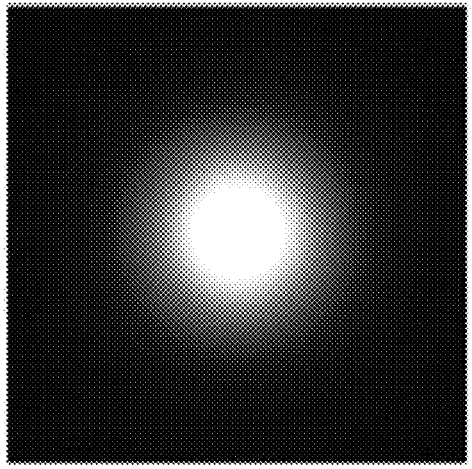
FIG. 1A　　　　　　　　FIG. 1B
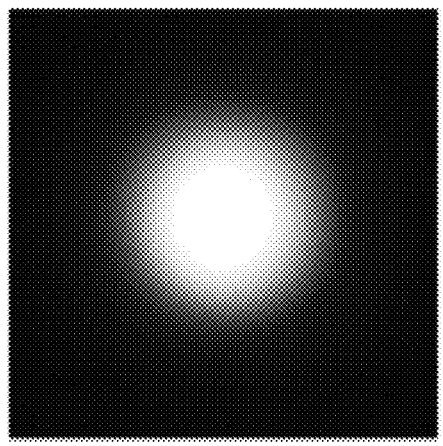
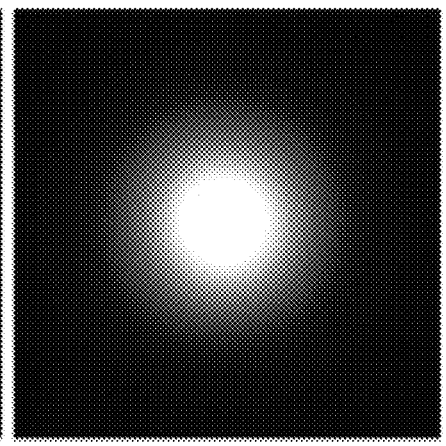
FIG. 1C　　　　　　　　FIG. 1D

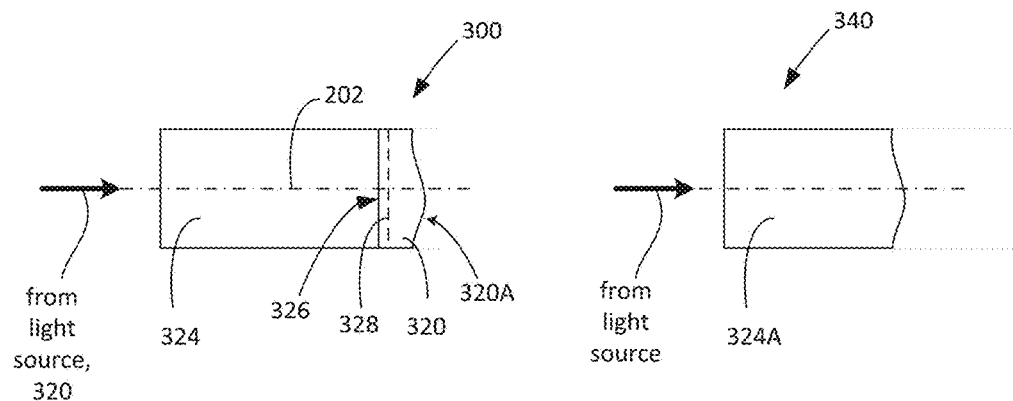
FIG. 3A
FIG. 3B
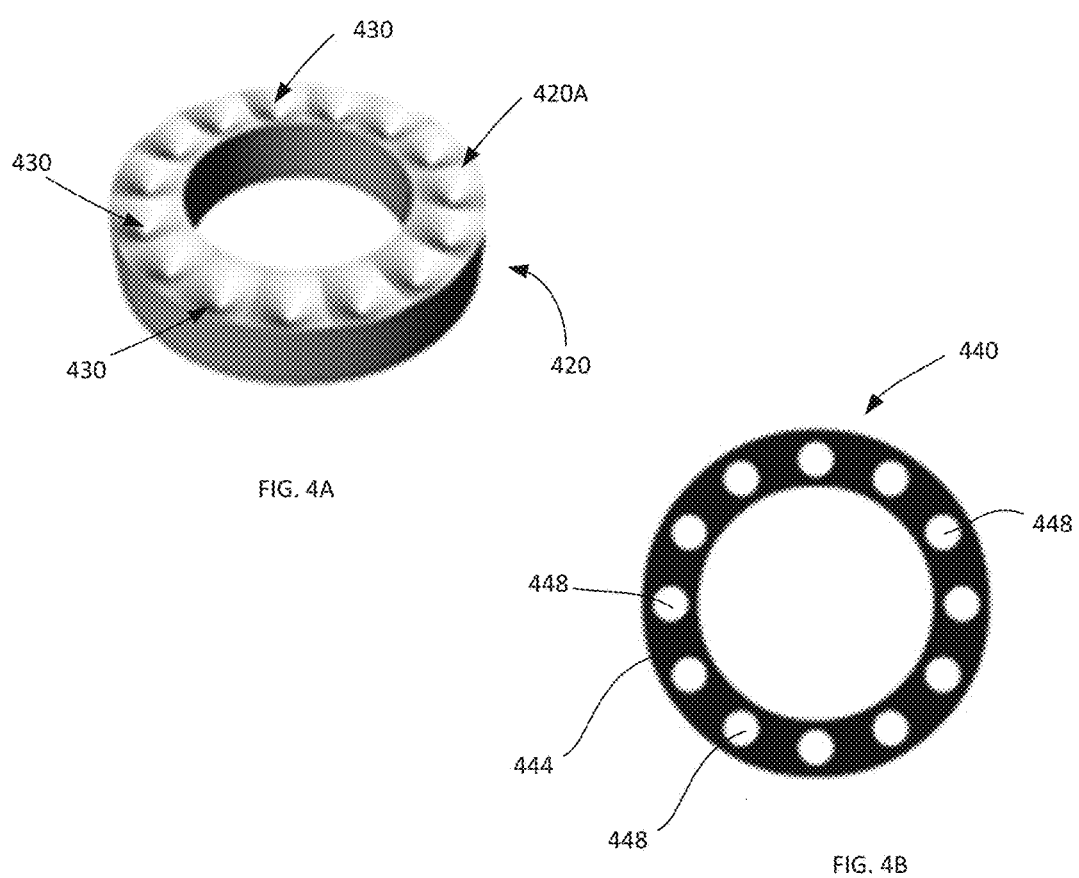
FIG. 4A
FIG. 4B

OPTICAL ARTICLE AND ILLUMINATION SYSTEM FOR ENDOSCOPE

CROSS-REFERENCE TO RELATED APPLICATIONS

This patent application claims priority from and benefit of the U.S. Provisional Patent Application No. 62/315,423, titled "Laparoscope Illumination System" and filed on Mar. 30, 2016. The disclosure of the above-identified provisional application is incorporated herein by reference.

GOVERNMENT LICENSE RIGHTS

This invention was made with government support under Grant No. R01 EB018921, awarded by National Institutes of Health. The government has certain rights in the invention.

TECHNICAL FIELD

The present invention relates generally to illumination systems for endoscopes, and more particularly, but not exclusively, to an illumination system (of an endoscope) equipped with an aspherical lens array.

RELATED ART

Endoscopes are instruments configured to be introduced into a body to provide a view of its internal parts. Laparoscopes, in particular, are commonly used to visualize lesions within internal organs with high resolution and allow a user to perform minor and complex surgical procedures with a few small incisions in the abdomen. To perform its functions, a laparoscope is typically equipped with an illumination system and an imaging system. The illumination system of the laparoscope serves the purpose of delivering light, emitted from a source of light, to a chosen object to be illuminated (such as an organ in the abdomen), typically by delivering such light through a lightguide component of the illumination system to the distal end of the laparoscope (for which an optical fiber bundle is often utilized). Light reflected from the illuminated object is then captured by the imaging system of the laparoscope, and delivered back to the proximal end, where the light is extracted to form an image of the object to be appropriately displayed for visualization and/or for data processing. FIGS. 1A, 1B, 1C, and 1D show three examples of differently-configured laparoscopes, along with the illumination patterns produced by light channeled through the corresponding imaging systems of these three laparoscopes on an acrylic sheet separated from the corresponding distal end by about 150 mm.

State-of-the-art laparoscope illumination systems, however, are subject to several shortcomings. The first stems from the narrow field-of-view (FOV), which is limited by the numerical aperture of the lightguide of the illumination system. The second operational drawback is caused by the fact that the spatial distribution of radiative energy emitted from the output end surface of the illumination system is highly non-uniform: most energy is concentrated in a small region at the center of the illumination field and the irradiance characteristic dramatically decreases from the center to the edge of the illumination field. As a result, most of the area of the illuminated object (a bodily organ, for example) cannot be clearly observed due to the poor performance of such an illumination system, especially the portions at the center and/or the edge of the illumination field. In addition, attempts to improve the optical performance of laparoscopes equipped with the conventional illumination systems by increasing the resolution of the imaging system are not necessarily successful due to inadequate illumination rendered by conventional illumination systems.

These drawbacks become even more operationally-limiting in the case of laparoscopes, the imaging systems of which are intended to capture light returning from a large surgical area. For instance, the operation of a multi-resolution foveated laparoscope, which is capable of capturing and relaying light with its imaging system both in a wide-angle and with high-magnification simultaneously for improved situational awareness, is substantially impeded due to its conventionally-structured illumination system that limits the utility of the wide-angle view due to the poor quality of illumination of the object at large field angles. There remains an unsatisfied need, therefore, in increasing the FOV of the illumination system of a laparoscope and improving the uniformity of irradiance provided by such system across the entire FOV.

SUMMARY

Embodiments of the present invention provide a system and method for overcoming the operational challenges faced by the currently used conventionally-structured endoscopes.

An embodiment of the illumination system of the endoscope according to the invention provides an article of manufacture including an optically-transparent component with a thickness defined between first and second surfaces of the component; each of these surfaces is transverse to the optical axis of the component. One of these surfaces carries a plurality of indentations that are located along a closed curve that circumscribes the optical axis, while another of these surfaces is planar. Such curve may represent an ellipse. The optically-transparent component may be generally shaped as a tubular element (in one case—a ring) of material, while the indentations have a specific cross-sectional profile, which in a specific implementation is chosen to ensure that each of the indentations defines a corresponding aspheric surface such that the article of manufacture as a whole contains an annular array of aspheric lenslets that encircles the optical axis.

Embodiments also provide an article of manufacture comprising (i) an optically-transparent component that has an optical axis and a thickness defined between first and second surfaces each of which is transverse to the optical axis. One of the first and second surfaces contains a plurality of indentations disposed along a closed curve that circumscribes the optical axis.

Embodiments further provide a lens system that includes a tubular element having an outer diameter, and inner diameter, first and second surfaces disposed in a spatially-separated and parallel relationship. The tubular element also has a first optical axis perpendicular to the first surface, and a thickness defined between the first and second surfaces. The tubular element is made of an optically-transparent material. The second surface is configured to define, in the tubular element, a multiplicity of aspheric lenslets each having a negative optical power and a corresponding optical axis. The points of intersection between optical axes of such lenslets and the second surface are located on a closed curve that is centered at the first optical axis.

BRIEF DESCRIPTION OF THE DRAWINGS

The invention will be more fully understood by referring to the following Detailed Description of Specific Embodiments in conjunction with the Drawings, of which:

FIG. 1A shows three endoscopes each containing a corresponding fiber-optic based illumination system;

FIGS. 1B, 1C, and 1D illustrate respective examples of the illumination patterns produced by the laparoscopes 1, 2, and 3. The illumination patterns were recorded on an acrylic sheet with the size of 500 mm×500 mm at a lighting distance of 150 mm;

FIGS. 3A, 3B provide schematic diagrams of embodiments of the invention;

FIG. 4A shows a perspective view of an article of manufacture configured according to the idea of the invention;

FIG. 4B shows a component of an embodiment of the invention configured as an opaque screen with a plurality of optical apertures;

FIG. 15A: a normalized illuminance distribution. FIG. 15B: a normalized intensity distribution.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

Figure 1E:
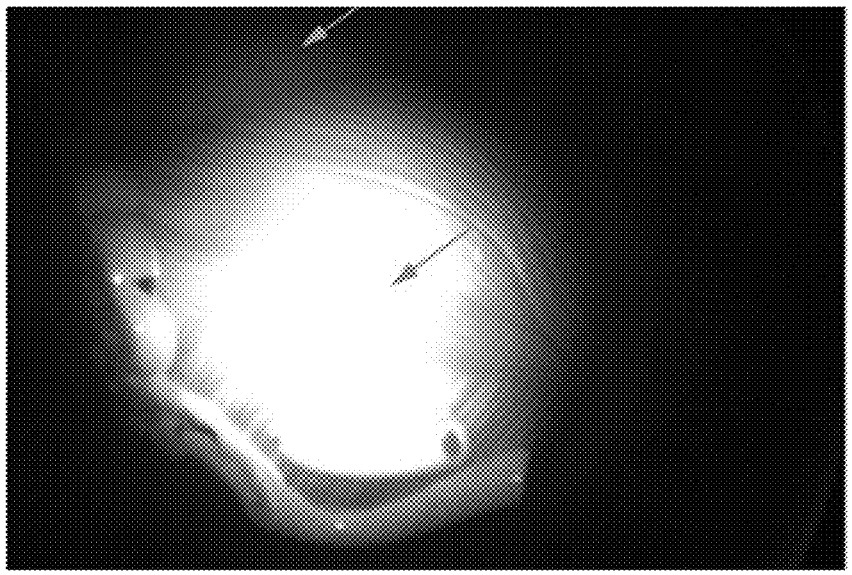
FIG. 1E shows an image of an object illuminated with a light distribution shown in one of FIGS. 1B, 1C, 1D. Most of the object cannot be clearly observed, especially at the center and the edge of the field.

While the following disclosure illustrates the details and features of embodiments of the invention in reference to specific examples—and, in particular, to examples of an endoscope configured as a laparoscope—it is appreciated that embodiments of the invention are structured for use with endoscopes in general, and that such use is within the scope of the invention. In a typical endoscope, the illumination system or portion of it accepts light (arriving from the light source disposed in optical communication with the proximal end of the laparoscope) with a lightguide (in some cases formed by an optical-fiber bundle) and channels or guides this light towards the facet of the lightguide formed at the distal end of the endoscope (the one facing the target during the operation of the device) to irradiate the target. The spatial distribution of light emitted from the output end facet of the illumination system of the endoscope resembles that of the output end facet itself. For that reason, the spatial distribution of light emitted from the output end facet of the illumination system of the laparoscope has a substantially uniform annular cross-sectional profile in the immediate vicinity of the output end facet. From the illumination engineering point of view, the output end surface of the lightguide (an optical-fiber bundle, in a specific case) is considered to be a secondary light source. As light emitted by the output end surface propagates towards the target, the light distribution tends to provide higher irradiance in the central area of the illuminated field, and lower irradiance (poor illumination) in the outer portions of the FOV, thereby forming a spatially non-uniform illumination field. (See, again, FIGS. 1B, 1C, 1D.) FIG. 1E shows a model of an internal organ that is rather unsatisfactorily—in terms of uniformity—illuminated with a light output form a laparoscope of FIG. 1A. The arrows in FIG. 1E point to the better and worse illuminated portions of the model. One can easily observe that most of the area of the organ model cannot be clearly seen, especially at the center and the edge of the model, under a typical illumination conditions provided by conventionally-configured laparoscopes.

Embodiments of the present invention address this problem of insufficient spatial uniformity of the illumination (irradiation) of a target with light delivered to the target with the use of a typical laparoscopic system (laparoscope), and corrects such inferior distribution of light energy across the target from being concentrated in the central portion of the light field to the one in which irradiance across the field is substantially more uniform. The solution is achieved by transforming the illumination system of the laparoscope via adding a judiciously chosen spatial distribution of optical power across the output (distal) end of it. Such physical transformation is carried out by either complementing the distal end of the illumination system with a specifically-formatted optical component or changing the profile of the output end facet of the lightguide of the illumination system, or—in some cases—both.

Figure 2:
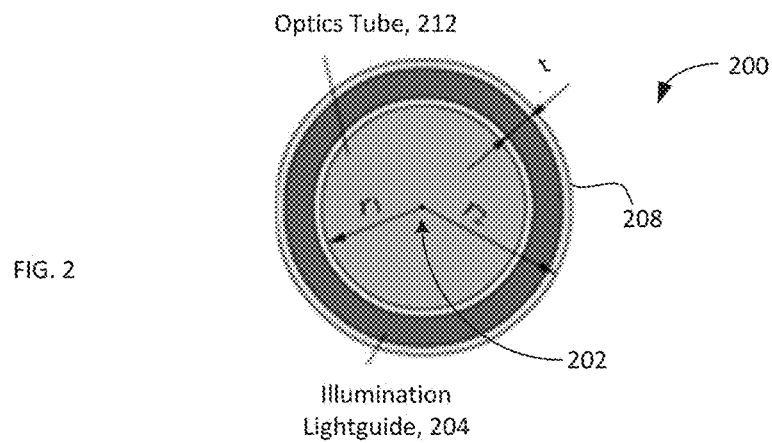
FIG. 2 schematically illustrates a cross-sectional view of a laparoscope of FIG. 1.

A cross-section 200 (made across a distal end of one laparoscope perpendicular to its axis shown as 202) is schematically shown in FIG. 2A. Here, a portion of the illumination system containing an annularly-shaped (in cross-section) lightguide 204 is shown contained between the outer sheath 208 of radius $r_2$ and the inner hollow structure 212 of radius $r_1$, referred to as an optics tube. The thickness of the annular wall of the lightguide, t, is defined by the difference in the radii values. The output distribution of light at the end facet of such laparoscope is represented by the uniform-irradiance annulus of light corresponding to the annular cross-section 204.

The idea of the invention stems from the realization that improvement of the uniformity of the illumination of the target in a plane transverse to the axis 202 can be achieved by judiciously formatting the shape of the output end facet of the illumination system of the laparoscope. The "shaping" can be effectuated, in one example, by adding an auxiliary optically-transparent component 320 (which has the distal surface 320A shaped according to the judicial design) to the distal end of the laparoscope 324 to "cap" the output end facet of the lightguide 204. This is schematically illustrated by the embodiment 300 in FIG. 3A. An additional optional component may be disposed between the unit 324 and 320 (shown by the dashed line 328). In another example of the implementation 340, the (otherwise flat) output facet of the lightguide 204 itself can be appropriately re-shaped, as shown in side view in FIG. 3B, to transform the laparoscope with an otherwise flat output facet of the lightguide into a laparoscope 324A in which the output end facet of the lightguide is curved according to the pre-determined design.

Therefore, according to the idea of the example of FIG. 3A, the lightguide of the laparoscope is complemented with the optically-transparent component 320 that has an optical axis and a thickness defined between first surface and second surface (surface 324A). Each of the first and second surfaces is transverse to the optical axis. In the simplest case, the component 320 is configured as a specifically-shaped plate made of optical material.

One non-limiting implementation 420 of such component with the distal curved surface 420A is presented in FIG. 4A. Here, as shown, the surface 420A contains a plurality of indentations 430, the centers of which are disposed along a closed curve that is contained in the surface 420A and that circumscribes the optical axis of the component 420. Another surface of the component 420 (the one, which in cooperation with the illumination system of the laparoscope is placed to face the output end surface of the lightguide 202) is generally planar.

It can be seen in FIG. 4 that the plate 420 has a cross-section defined in a plane that is transverse to the optical axis of the component. The cross-section has a perimeter defined by a differentiable closed curve. Generally, the form of the perimeter of the plate 420 corresponds to the perimeter of the lightguide 204. In one specific implementation, such close curve is an ellipse 434. In a related embodiment, the closed curve can contain angles. In a specific embodiment, the article of manufacture formed by the component 420 is complemented with a correspondingly-shaped screen element 440 (shown in FIG. 4B in front view) that has an optically-opaque area 444 and a plurality of optically-transparent apertures 448, the number and positioning of which directly corresponds to those of the indentations 430 of the component 420 such that, when the components 420 and 440 operably cooperate with one another, the indentation 430 and the aperture 448 are spatially co-registered. In this case, when the components 420, 440 are assembled together, light passing through the apertures 448 also passes through the indentations 430.

Figure 5A:
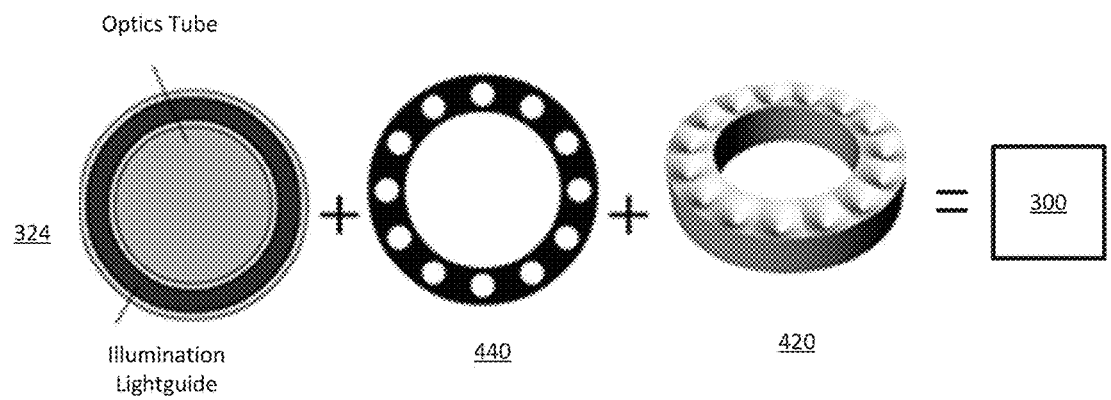
FIG. 5A schematically illustrates a combination of components aggregately forming the embodiment of the invention of FIG. 3A.
Figure 5B:
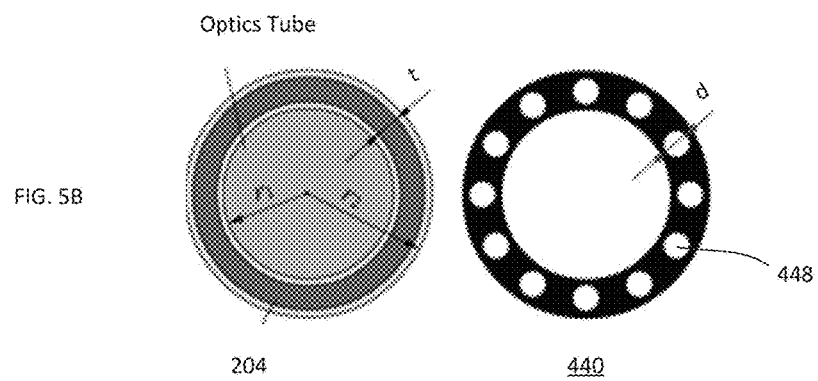
FIG. 5B schematically illustrates another combination of the components forming an embodiment of the invention. Presented are a cross-sectional view of a laparoscope and an optically-opaque screen with an array of apertures.

To this end, the optically-transparent component 420 defines a first projected area on a plane that is transverse to its optical axis. The screen 440 is appropriately dimensioned to define a second projected area on the same plane such that the first and second projected areas are congruent with one another. It is understood that two figures or objects are congruent if they have the same shape and size, or if one has the same shape and size as the mirror image of the other. The term projected area is used to refer to a two-dimensional area identified by a three-dimensional object on an arbitrary plane as a result of projecting the shape of such object on to this arbitrary plane. The optical communication of the laparoscope 324 of FIG. 3A with the components 420 and 440 is schematically shown in FIG. 5A. Here, the result of assembly of the components 324, 440, 420 results in a laparoscope the lightguide element of the illumination system of which is in optical communication with the optically-transparent component 420A through the screen 440. It, is readily appreciated by a skilled artisan, that the screen 440 is judiciously co-dimensioned not only with respect to the component 420, but with respect to the cross-section of the illumination system of the laparoscope (with which the component 420 is intended to be used) as well. This is illustrated in FIG. 5B, where d=t, and the inner radius of the screen 440 is equal to while the outer radius of the screen 440 is equal to $r_2$. (In a related embodiment, where the screen 440 is not employed, an article of manufacture was formed in which the output end facet of the lightguide 204 abuts directly against the optically-transparent component 420; not shown.)

From the optical point of view, the component 420 represents a lens system that includes a tubular element having outer and inner diameters as well as first and second surfaces that are disposed in a spatially-separated and parallel relationship with respect to one another. The length or thickness of such lens system is defined between the first and second surfaces of the lens system. The tubular element is made from an optically-transparent material. The second surface (the surface of system 420 that contains indentations 430) is configured to define a multiplicity of lenslets, one surface of each of which has a shape corresponding to the shape of the corresponding indentation 430. According to one implementation, as discussed below, each of the lenslets has an aspheric surface and a corresponding negative optical power. In reference to the schematic of FIG. 4A points of intersection between optical axes of such lenslets and the second surface of the lens system 420 are located on a closed curve that is centered at the optical axis of the lens system 420. As long as the area of the second surface of the lens system 420 that correspond to a given indentation 430 has a cross-sectional profile deviating from a curve having the same value of the radius of curvature at any point of such curve, the corresponding lenslet defines an aspherical lenslet. In a specific case when each of the indentations 430 defines a corresponding aspherical lenslet, the lens system 420 represents an array of aspherical lenslets disposed along a perimeter of the system 420.

Referring again FIGS. 3A, 5A, and 5B, in practice the array 420 of aspheric lenslets together with the screen 440, containing an array of apertures 448, are placed next to and coaxially with the distal surface of the laparoscope to appropriately redistribute light 320 across the target (not shown) that faces the distal end of the laparoscope, to produce a desired quality illumination over an extended area of the target. It would be readily appreciated that, as a result of using the aperture array 440, the annular non-Lambertian secondary light source defined by the light distribution at the flat output end facet 326 of the lightguide 204 is divided into several non-Lambertian disk-shaped light sources. Each of such disk-shaped light sources is defined by a corresponding aperture opening 448. In the case when these non-Lambertian disk-shaped sources of light are substantially congruent, the spatial energy distribution produced by each disk-shaped light source from the energy carried in the beam 320 is redistributed by a respectively-corresponding lenslet of the lens system 420 towards the target to form the desired target-illumination field with desired degree of spatial uniformity. In particular, the resulting illumination field produced by the lens system 420 has a wider field of view, FOV (as compared to that produced by the conventional, flat output end facet of the lightguide 204), and is defined at least in part by the sum of all individual, constituent light outputs produce d by the individual lenslets from the array of lenslets.

A design of the component 420 should satisfy the dimensionality requirement dictated by the very limited space provided by the distal end of the laparoscope. The combination of the lens system 420 with the screen 440 should be as compact as possible, while at the same time maximizing the number of light rays passing through each of the apertures 448 to achieve high energy efficiency.

The discussed below approach to the design of an individual, constituent lenslet of the lens system 420 includes an illumination design prescribed for an extended non-Lambertian source having three-dimensional (3D) rotational geometry. Usually, zero-etendue design methods that rely on the assumption of a point source or a collimated beam of light fall short from providing good designs, in which the influence of the size and/or angular extent of a real, practical source of light on the performance of an illumination system cannot be ignored.

To carry out the design of an embodiment of the invention, a specific "feedback method" was developed for an extended non-Lambertian source in a 3D rotational geometry. The design process of the array 420 of aspherical lenslets in accordance with the embodiment of the present invention includes the following six steps:
1. Characterizing the irradiance or luminance distribution of the outgoing beam outcoupled directly from the optical-fiber bundle of the conventional laparoscope.
2. Determining of a profile of a constituent aspherical lenslet in a meridian plane, which allows achieving a desired intensity distribution.
3. Constructing of a 3D model of the constituent aspherical lenslet by applying rotation to the curve describing the determined profile of the lenslet, and performing a Monte Carlo ray-tracing to calculate the actual intensity distribution of the model of the lenslet.
4. Defining an intensity feedback function based on the difference between the actual intensity distribution and the desired one, and calculate a new intensity distribution by using the feedback function.
5. Repeating steps (2)-(4) to meet the predefined stopping or tolerance criteria. Forming the array of aspherical lenslets by rotating one aspherical lenslet about the optical axis of the laparoscope at a set of discrete angles.

Step 1:

Characterization of the Distribution of Irradiance or Luminance of the Outgoing Beam.

Referring again to FIGS. 2 and 5B, schematically illustrating a cross section of the body of the laparoscope used as an example, $r_1$ and $r_2$ respectively represent the radius of the optics tube and the outer radius of the laparoscope's sheath. The quantity t represents the thickness of the annular fiber bundle, which equals the diameter d of each opening on the aperture screen 440. The values of these parameters are summarized in Table 1.

Figure 6:
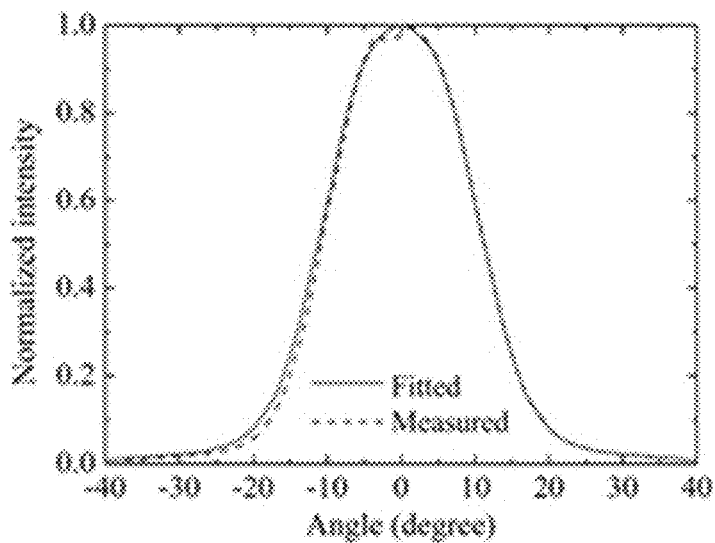
FIG. 6 includes plots illustrating a normalized intensity distribution of a beam of light outcoupled from the laparoscope 1 of FIG. 1A. The dashed line represents the intensity distribution; the solid line represents the distribution of intensity obtained from data fitting, used in for design of an embodiment of a lens system of the invention.

The intensity distribution of the outgoing beam from the lightguide 204 (in one case the optical-fiber bundle) of one of the laparoscopes of FIG. 1A was measured with spectroradiometer, and the measured normalized intensity distribution of it is shown in FIG. 6 with the dashed line. The empirically0-acquired distribution clearly shows the dramatic decrease of intensity with increase of the emission angle of the outgoing ray, which indicates that the secondary light source formed by the output end facet of the lightguide 204 is a space-invariant non-Lambertian source of light.

An even polynomial curve was fitted to the measured data, which is denoted by the solid line in FIG. 6.

For the purposes of fitting, the following equation was used:

$$I(\theta) = \sum_{m=0}^{15} a_m \theta^{2m}, \quad (1)$$

$$0 \leq \theta \leq \theta_{max},$$

where $I(\theta)$ denotes the intensity distribution of the outgoing beam from the lightguide 204, $\theta$ is the solid angle variable associated with the outgoing beam in radians, and $\theta_{max}$ is the maximum solid angle of the outgoing beam. The polynomial coefficients are provided in Table 2 below. The luminance distribution, $L(\theta)$, of the outgoing beam exiting from each opening can be calculated by $$L(\theta) = \frac{I(\theta)}{2d\cos\theta}, \quad (2)$$

$$0 \leq \theta \leq \theta_{max}.$$

TABLE 1

| Parameters | Comment | |
|---|---|---|
| H | z-coordinate of point $C_1$ | 1.5 mm |
| T | Thickness of the annular fiber bundle | 0.8 mm |
| D | Diameter of each opening on the aperture | 0.8 mm |
| $r_1$ | Radius of the optics tube | 3.2 mm |
| $r_2$ | Outer radius of the laparoscope | 5 mm |
| N | Index of refraction | 1.4935 |
| TOL | Stopping criteria | 0.01 |
| $\theta_{max}$ | Maximum direction angle of incident ray | 40° |
| $\beta_{max}$ | Target maximum direction angle of outgoing ray | 50° |

TABLE 2

| Coefficients | comment | |
|---|---|---|
| $a_0$ | $\theta^0$ | 0.999007437522762 |
| $a_1$ | $\theta^2$ | −9.63852733603546 |
| $a_2$ | $\theta^4$ | −305.799307137239 |
| $a_3$ | $\theta^6$ | 8830.45725424946 |
| $a_4$ | $\theta^8$ | −106591.691828219 |
| $a_5$ | $\theta^{10}$ | 751880.112289806 |
| $a_6$ | $\theta^{12}$ | −3323375.40520153 |
| $a_7$ | $\theta^{14}$ | 9071490.09980684 |
| $a_8$ | $\theta^{16}$ | −13347885.4644803 |
| $a_9$ | $\theta^{18}$ | 3156692.8836402 |
| $a_{10}$ | $\theta^{20}$ | 20923881.7914922 |
| $a_{11}$ | $\theta^{22}$ | −24470937.1348521 |
| $a_{12}$ | $\theta^{24}$ | −7365642.41767329 |
| $a_{13}$ | $\theta^{26}$ | 22577043.2048786 |
| $a_{14}$ | $\theta^{28}$ | −2.65285732815084 |
| $a_{15}$ | $\theta^{30}$ | −8808674.8720653 |

Steps 2 Through 5:
Design of the Cross-Section Profile the Individual Constituent Lenslet of the Array.

Figure 7:
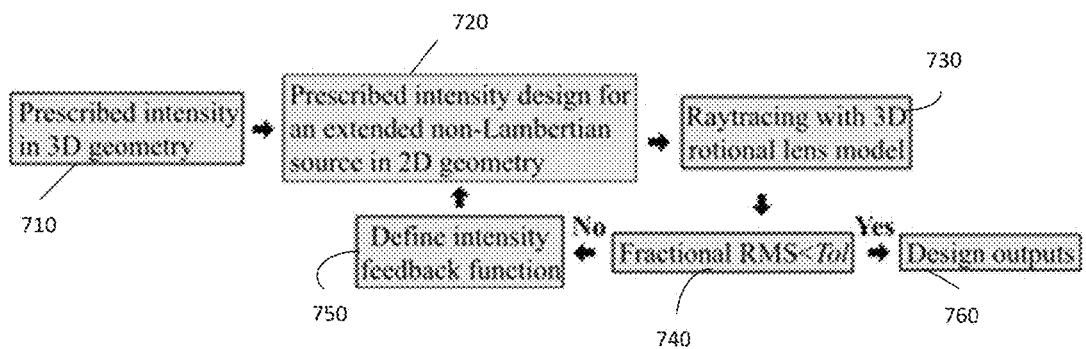
FIG. 7 is a flow-chart illustrating a feedback method for design of an extended non-Lambertian source in a 3D rotational geometry.

A version of the process for designing the lens profile of the individual lenslet is summarized with the flowchart of FIG. 7.

Given a prescribed 3D intensity distribution, 710 (such as the one measured from the output of the lightguide, FIG. 6), a two-dimensional (2D) lens shape is determined for the extended non-Lambertian source that has this prescribed intensity at step 720. This is done, for example, with the help of a prescribed illumination design for an extended non-Lambertian source in three-dimensional (3D) rotational geometry (see Wu et al., "Direct design of aspherical lenses for extended non-Lambertian sources in two-dimensional geometry," Opt. Lett. 40, 3037-3040 (2015), the disclosure of which is incorporated by reference herein). Then a 3D model of the individual lenslet is generated by rotating the 2D lens profile and analyzing the 3D performance of the lenslet with ray-tracing, 730. Finally, a "feedback method" is employed to further improve the optical performance until the predefined stopping criterion is met, at steps 740, 750, and 760.

One of the important features the feedback method is achieving the prescribed design for the extended non-Lambertian source in 2D geometry.

Figure 8:
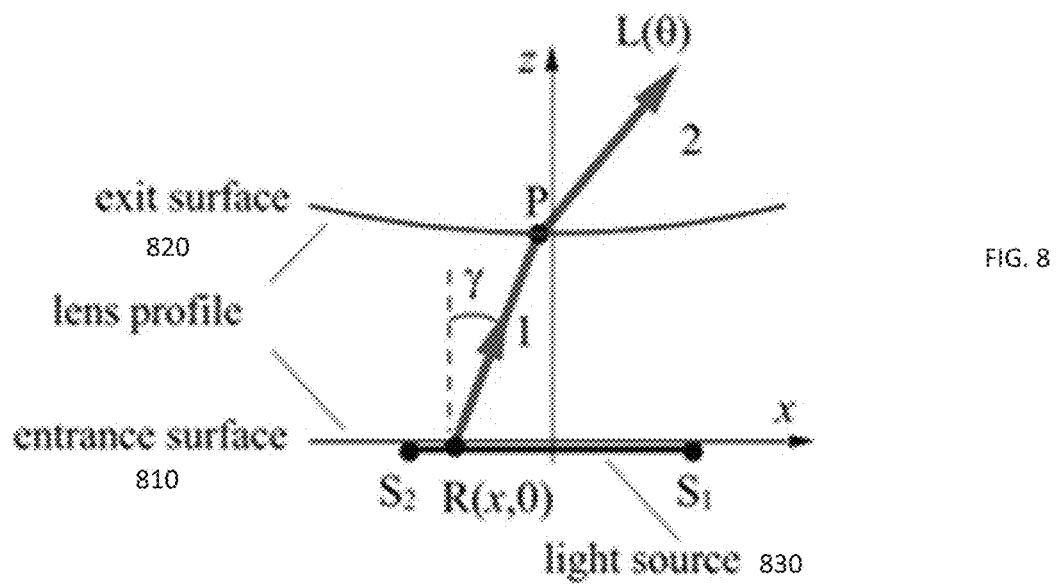
FIG. 8 schematically illustrates an example of cross-sectional profile of surfaces of an individual aspherical lenslet configured in accordance with the idea of the present invention.

The following considerations were taken into account: the entrance (proximal) surface 810 of the lens system 420 was assumed to be a planar surface; the exit (distal) surface 820 of an individual lenslet 430 was assumed to be a curved aspherically shaped surface; and the extended light source 830 was considered to be in optical communication with the entrance surface 810, as illustrated in FIG. 8.

The sequence of design steps is now discussed in more detail. A single ray originating from the light source is first refracted by the entrance surface at an angle γ, and then further refracted by the exit surface at an angle θ. The direction angle of such ray after refraction at the entrance surface satisfies the condition of $$n \cdot \sin(\gamma_{max}) = \sin(\theta_{max}).$$

The individual aspherical lenslet of the lens system is assumed to be loss-less, (that is, the luminance of the incident rays is assumed to be conserved upon the propagation through the lenslet). Then, the total flux emitted from the light source is given by $$\Phi_1 = \int_{\theta_{min}}^{\theta_{max}} \int_{-d/2}^{d/2} nL(\theta)\cos\theta \, dx d\theta, \quad (3)$$

where n is the index of refraction of the lens unit (lenslet). The prescribed output intensity distribution is expressed as $I_t(\beta) = K/\cos 3\beta$, with a directional angle β of propagation of the rays ranging between $\beta_{min} \leq \beta \leq \beta_{max}$ (here, $\beta_{min} = -\beta_{max}$). According to the conservation law of energy, the total flux of the outgoing beam is equal to that of the incident beam. Therefore, $$\Phi_1 = \int_{\beta_{min}}^{\beta_{max}} I_t(\beta) d\beta. \quad (4)$$

K is a constant which can be calculated by applying energy conservation.

Figure 9A:
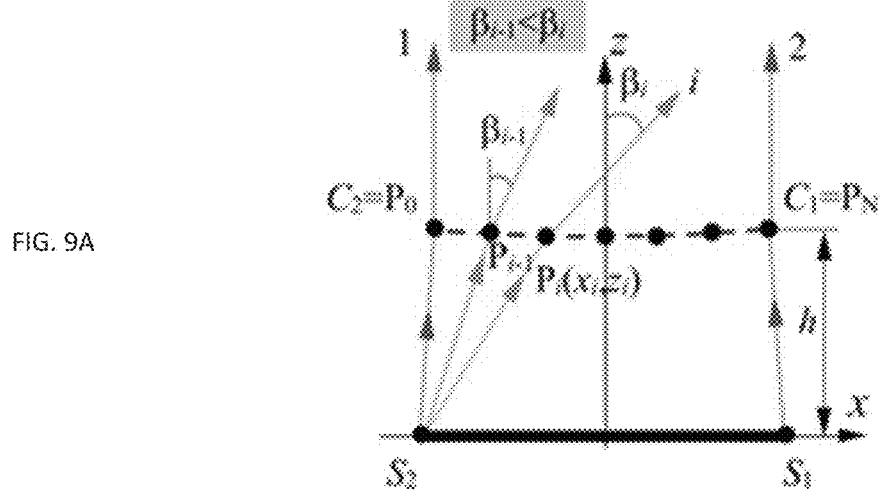
FIGS. 9A, 9B, and 9C illustrate the monotonically-increasing function $\beta=f(x)$ (FIG. 9A), the calculation of a first-approximation cross sectional profile of an individual indentation of an output surface of the element representing the embodiment of the lens system (FIG. 9B), and the process of calculation of the rest of such profile (FIG. 9C) in accordance with the idea of the present invention. Here, "h" represents a z-coordinate of point C1.

Due to the nature of a spatially extended source of light 830, an initial patch (that is, a first approximation) of the profile of the surface 820 is required for the design. In FIG. 9A, the curve C1C2 represents such initial patch. Here, C2 is a mirror point of C1 about the z-axis. The two edge rays, S1C1 and S2C2, should be refracted by the initial patch to have the resulting direction angle β=0° upon leaving the exit surface of the initial patch. An edge ray emitted from S2 passes through an arbitrary point Pi on C1C2 and propagates further at the direction angle βi. To ensure a successful design, it is required that $\beta_{i-1} < \beta_i$. Here, $\beta_{i-1}$ is the direction angle of the propagation of the outgoing ray at the previous point Pi-1, as shown in FIG. 9A.

Figure 9B:
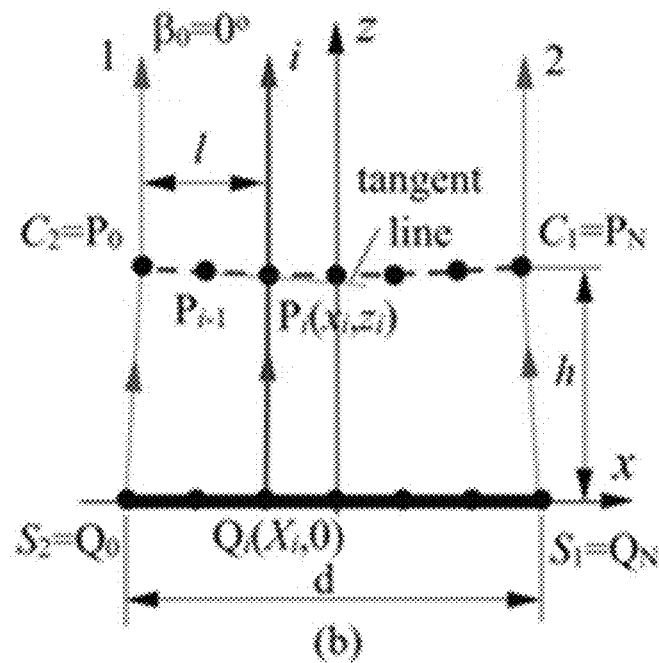

When the direction angle, β, of the outgoing ray can be represented mathematically by a monotonically increasing function β=f(x), the condition dβ/dx>0 is satisfied on the initial patch C1C2, To achieve this, a set of data points on C1C2 and S1S2, respectively, is defined, with the point that are equally spaced along the x-axis. In addition, the incident rays $Q_iP_i$ (i=0,1, ..., N) are directed to exit the initial patch at β=0°, as shown in FIG. 9B. As a result, a set of outgoing rays is directed parallel to the z-axis between the two edge rays, 1 and 2. Since the incident rays corresponding to these outgoing rays are predefined, the luminance of these outgoing rays is known. As a result of these outgoing rays being parallel to each other, the luminance of these outgoing rays between the two edge rays 1 and 2 can be represented as a function of the distance l (the distance between the outgoing ray i and the edge ray 1, as shown in FIG. 9B). The function for the luminance distribution satisfies $L_0 = f_0(l)$ ($0 \leq l \leq l_0$). Here, $l_0$ denotes the distance between the two edge output rays (ray 1 and ray 2). Then, the output intensity at direction β=0° is the integral of the function $L_0 = f_0(l)$ over the closed interval $[0, l_0]$, and given by $$I(0) = \int_0^{l_0} f_0(l) dl. \quad (5)$$

Figure 9C:
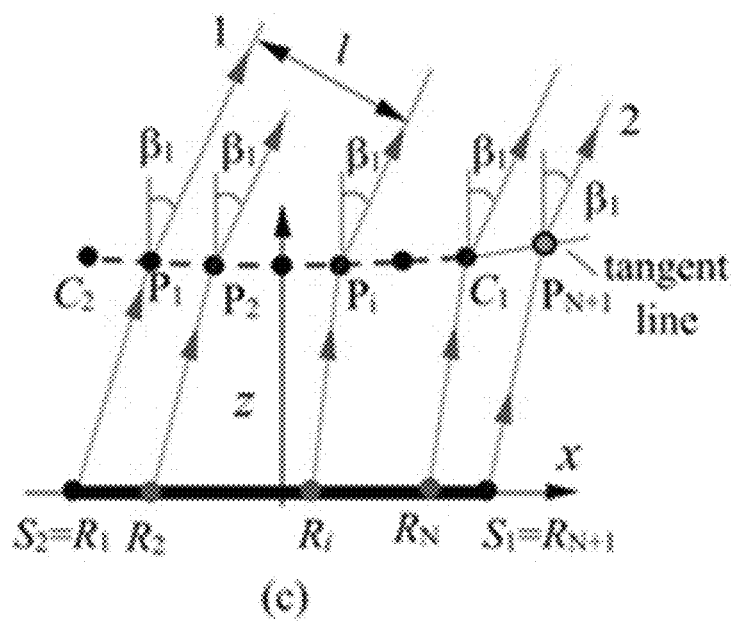

When the description of the initial patch is devised, the rest of the lenslet profile can be calculated. The calculation of a point $P_{N+1}$ is provided as an example. Here, the edge ray, S2P1, is traced and the direction angle $\beta_1$ of its outgoing ray (ray 1), shown in FIG. 9C, is calculated. Then, the determination of a set of points $R_i$ (i=2,3, ..., N) on the source S1S2 is performed. The points of the set $R_i$ points are chosen such that such that the rays $R_iP_i$ (i=2,3, ..., N) exit the initial patch C1C2 also in the direction corresponding to $\beta=\beta_1$. Once x-coordinates of points from the set $R_i$ has been obtained, the luminance of the corresponding outgoing rays can be calculated.

Further, a ray is traced from the point S1 of the light source, and the new point $P_{N+1}$ is calculated for the profile of the surface 820 as the point of intersection between the ray $S1P_{N+1}$ and the tangent to the profile at the previous point C1 ($P_N$), as shown in FIG. 9C. Suppose this ray exits the lens also in the direction defined by $\beta=\beta_1$. The luminance of the corresponding outgoing ray (ray 2), is known. As a result, a set of outgoing rays that are parallel to the two edge rays 1 and 2 is obtained, and similarly the luminance of these outgoing rays between the two edge rays 1 and 2 can be represented as a function of the distance l, for example as $L_1=f_1(l)$. Similarly, the output intensity $I(\beta_1)$ at an angular direction $\beta=\beta_1$ is the integral of the function $L_1=f_1(l)$ over the distance between the two edge rays 1 and 2 shown in FIG. 9C.

Next, the position of the point $P_{N+1}$ on the tangent to the profile at the point C1 is adjusted to make the output intensity $I(\beta_1)$ equal the prescribed intensity, $I_t(\beta_t)$. After such adjustment, the normal vector NN+1 is calculated with the use of Snell's law. The set of calculations described above is performed again until the direction angle of the incident ray from S1 satisfies the condition $\theta > \theta_{max}$. At the moment this tolerance or stopping condition is satisfied, the resulting profile of the curve 820 is considered to be a profile of the exit (distal) surface of the individual lenslet in a meridian plane.

Following the determination of such 2D design of the (aspherical) lenslet profile in the local meridian plane, the 3D model of the aspherical lenslet is generated by rotating the devised lenslet profile about a chosen axis. A Monte Carlo ray-tracing procedure is further performed to calculate the actual distribution of intensity at the output of the lenslet in 3D geometry. The prescribed intensity distribution $I_t(\beta)$, which can produce uniform far field illuminance in 3D geometry, should satisfy the condition of $I_t(\beta)=\cos 3\beta$ ($0 \le \beta \le \beta_{max}$), where $\beta_{max}$ is the desired maximum value of the direction angle of the outgoing ray from the exit surface 820 of the lenslet.

Figure 10A:
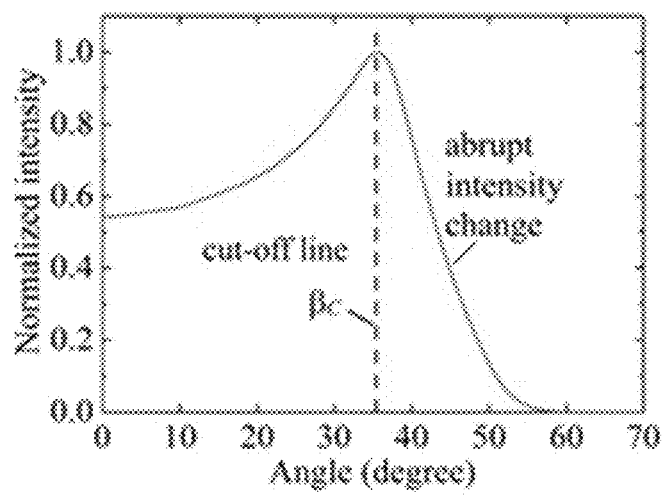
FIG. 10A illustrates a region of abrupt intensity change caused by the limitation of one single aspherical surface and the Monte Carlo raytracing.

If and when a good agreement between the prescribed intensity and the actual one produced by the 3D model cannot be achieved due to the presence of the skew rays that have not been considered in the 2D design, an alternative intensity feedback strategy is employed to improve the performance of the aspherical lens. To this end, let $\beta_C$ denote the maximum effective angle of the 3D design, as shown in FIG. 10A. Then, the feedback function is calculated in the region $[0,\beta_C]$. Let $I_i(\beta)$ be the actual 3D intensity distribution obtained from the i-th iteration. The feedback function is defined by $$\eta_i(\beta)=I_t(\beta)/I_i(\beta), \quad 0 \le \beta \le \beta_C. \tag{6}$$

Then, the target intensity distribution used for the (i+1)th iteration to design the lenslet profile is given by $$I_{t(i+1)}(\beta) = I_t(\beta) \times \prod_{j=0}^{i} \eta_j(\beta), \tag{7}$$

$$0 \le \beta \le \beta_C.$$

Thereafter, the polynomial fitting is performed to determine the target intensity distribution in the range $[0,\beta_{max}]$ after the intensity distribution in the range $[0,\beta_C]$ has been obtained by Eq. (7). The polynomial is expressed as $$I_{t(i+1)}(\beta)=a_2\beta^4+a_1\beta^2+a_0, \quad 0 \le \beta \le \beta_{max}. \tag{8}$$

With this new target intensity in the range $[0,\beta_{max}]$ the 2D design of the profile of the surface 820 is updated and the subsequent operations performed until the stopping criterion is met. Here, we employ the fractional RMS to quantify the difference between the actual intensity and the prescribed one:

$$RMS = \sqrt{\frac{1}{N}\sum_{k1=1}^{N}\left(\frac{I_{ak1}-I_{tk1}}{I_{tk1}}\right)^2}, \tag{9}$$

where N is the number of the sample points, $I_{tk1}$ is the target intensity of the $k_1$-th point defined by the prescribed intensity and $I_{ak1}$ is the actual intensity of the $k_1$-th point. A smaller value of RMS represents smaller difference (i.e. a better agreement) between the actual intensity and the prescribed one. Suppose the iteration stops when the tolerance condition RMS<Tol is satisfied, where Tol is a pre-defined value of the difference between the prescribed and obtained intensity distributions. The value of Tol is given in Table 1. Since the region of abrupt intensity change, shown in FIG. 10A with a dashed vertical line, cannot be eliminated due to the limitation of one single aspherical surface, a design is considered acceptable as long as the good agreement is achieved for the region within the range $[0,\beta_C]$. To make the effective control angle, $\beta_C$, close to the desired control angle (which equals 40°), $\beta_{max}$ is set at 50°.

Although the illumination design method described above is not limited to a particular type of the extended secondary illumination source formed by a lightguide portion of a laparoscope, the design of the individual lenslet (430 in FIG. 4A) and the resulting array of such lenslets (420 in FIG. 4A) depends at least in part on the profile of intensity distribution at the output from the end facet of the conventional lightguide of the illumination system of the conventional laparoscope.

Without loss of generality, an example of a lenslet array configured for use with the laparoscope 1 of FIG. 1A was produced, with the aim to form an illumination of the chosen object with a higher degree of uniformity that that produced by the laparoscope 1 alone. To this end, and referring again to the combination of the components that aggregately form an embodiment of the invention, as shown in FIG. 5A, each of the disk-shaped sources of light 448 formed by individual apertures of the aperture array contained in the screen 440 in practice has the same intensity distribution as the one shown in FIG. 6.

Figure 10B:
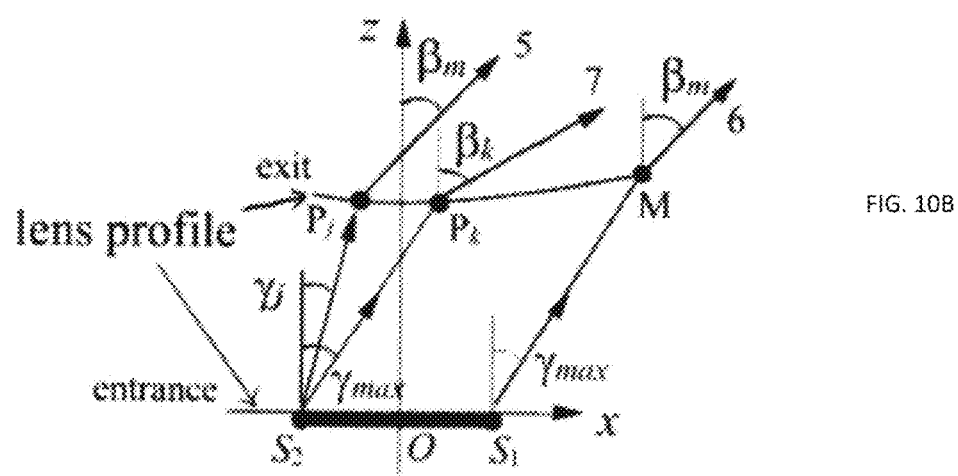
FIG. 10B illustrates $\gamma_{max}$, representing the maximum direction angle of the ray from point $S_1$ after the refraction at the entrance surface and $\beta_m$ is the direction angle of ray 6.

In order to obtain high energy efficiency, the diameter d of the circular aperture 438 was set to 0.8 mm (which was also the value of the diameter of the non-Lambertian disk-shaped source used in the subsequent design). The interior/inner radius, $r_1$, of the lens system 420 was set equal to 3.2 mm (as defined by the clear aperture of the laparoscope imaging system), while the exterior/outer radius $r_2$ of the lens system 420 was set to be less than 5.5 mm (which is by the packaging requirements of a typical conventional laparoscope). The half FOV of the imaging system of the laparoscope 1 was set at 40°. The goal was to form an aspherical lens system 420 that is capable of producing satisfactory illumination in the region [−40°, 40°]. Due to the limitation of one single aspherical surface used in the lens design, both the maximum effective angle $\beta_m$ obtained from the design of a 2D profile of the surface 820 and the maximum effective angle $\beta_C$ obtained from the 3D raytracing simulation were less than the prescribed maximum angle $\beta_{max}$, as shown in FIG. 10B. Thus, we let $\beta_{max}=50°$ to obtain good illumination in the range [−40°, 40°]. The refractive index of optically-transparent material of the lenslet was set to 1.4935. These design parameters are summarized in Table 1. In FIG. 10B the direction angle of ray 5 also equals $\beta_m$. Due to the limitation of one single aspherical surface, $\gamma_j<\gamma_{max}$, and $\beta_m<\beta_{max}$. In addition, an arbitrary ray emitted from $S_2$ at a direction angle θ with a value between $\gamma_j<\theta<\gamma_{max}$ propagates at a resulting direction angle β between $\beta_m<\beta<\beta_k$ (where $\beta_k$ is the direction angle of the ray 7). Usually, $\beta_k>\beta_{max}$.

Figure 11A:
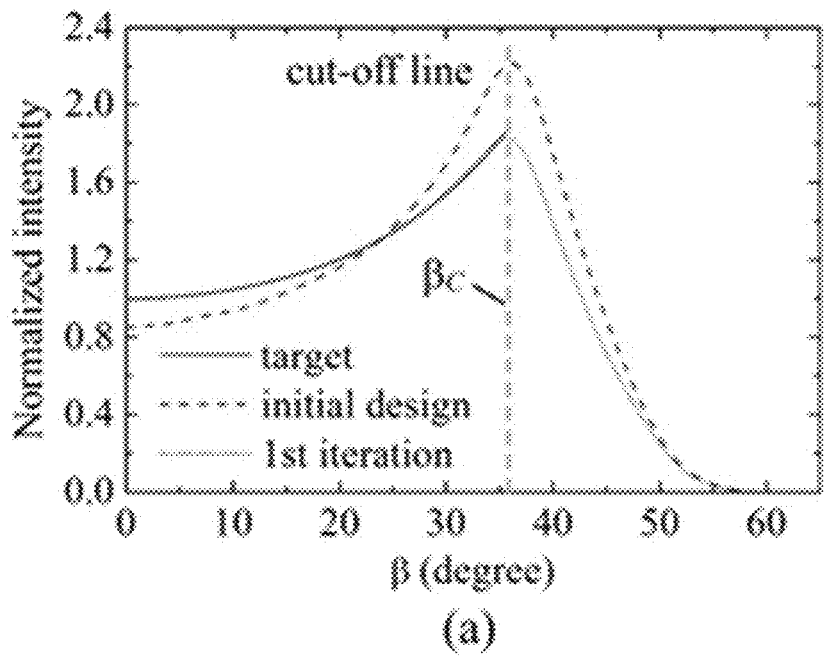
FIGS. 11A, 11B, 11C, 11D, and 11E illustrate a normalized intensity distribution (FIG. 11A), the target intensity distribution used in the initial design and the 1st literation (FIG. 11B), the illumination pattern obtained from Monte Carlo ray-tracing (FIG. 11C), the illuminance distribution along the line y=0 mm (FIG. 11D), and the profile of the aspherical lens unit (FIG. 11E)

FIG. 11A illustrates the intensity distribution (shown in a dashed line) at the output of the embodiment of FIGS. 3A, 5A formed according to the initial design of the screen 440 and the lens system 420. Because the actual intensity distribution deviated from the prescribed one (the RMS error of the initial design was determined to be 0.1054 in the range [0,$\beta_C$], $\beta_C$=35.54°), the feedback strategy discussed above was employed to improve the performance of the embodiment. In particular, five million rays were traced during each iteration. The feedback design converged with the stopping criterion being met after the 1st iteration. The polynomial coefficients of the feedback function are provided in Table 3. The profile of the optimized aspherical surface 820 is represented by an even polynomial curve, expressed as $$z = \sum_{m=0}^{20} c_m x^{2m}. \tag{10}$$

Figure 11B:
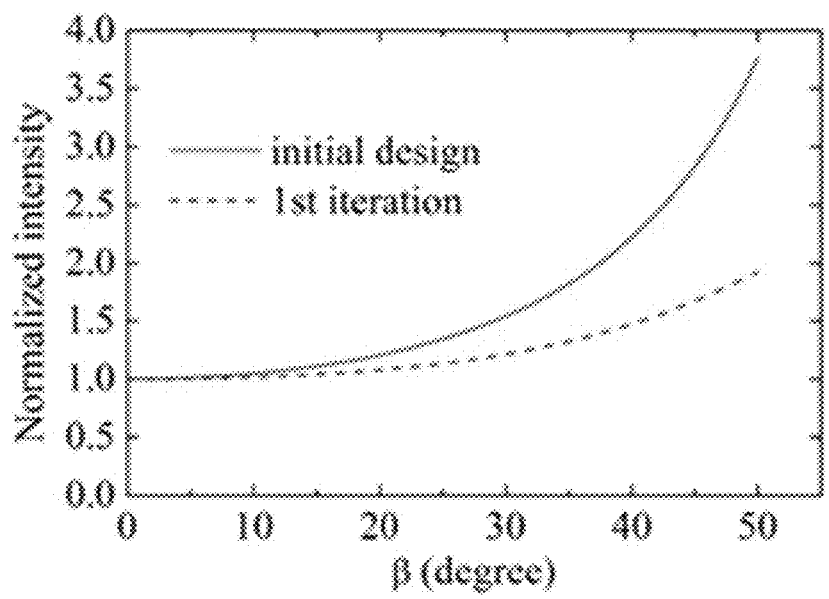
Figure 11C:
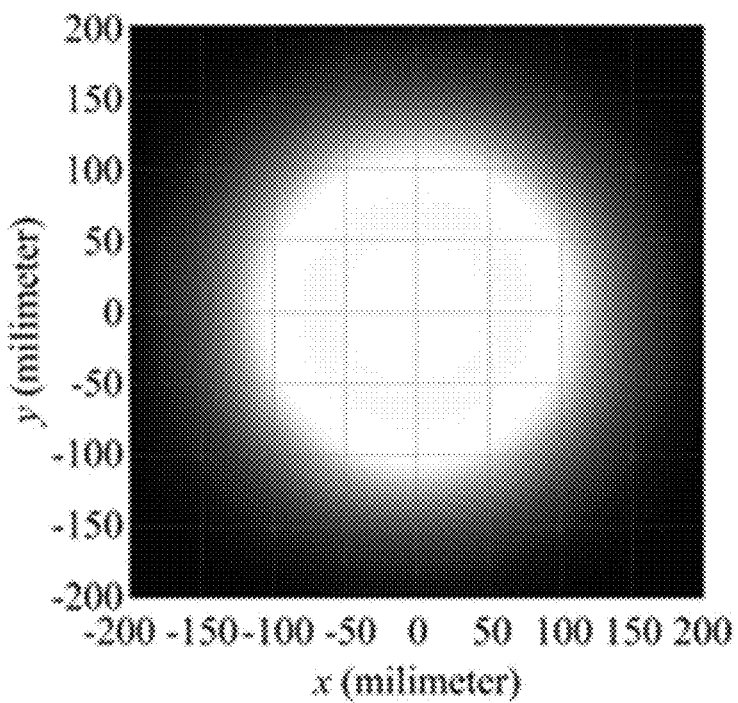
Figure 11D:
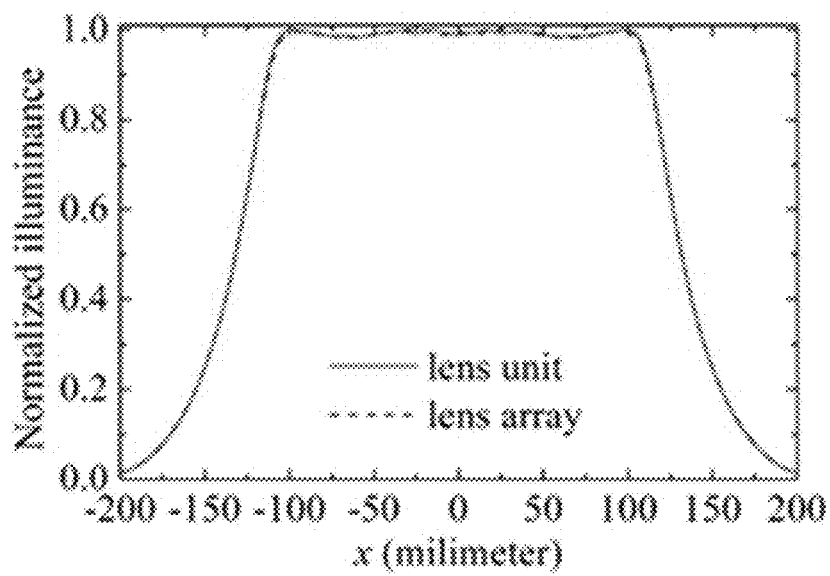

The polynomial coefficients are provided in Table 4. The intensity distribution obtained from the 1st iteration is shown in FIG. 11A with RMS of 0.0053. It clearly shows that good agreement is achieved on the region [0,$\beta_C$]. The updated target intensity used in the 1st iteration is given in FIG. 11B ($a_2$=0.8927, $a_t$=0.5350, and $a_0$=1). The difference between the target intensity used in the 1st iteration and the one used in the initial design can be observed. The illumination pattern obtained from simulation at a working distance of 150 mm from the output end facet of the embodiment of the invention is given in FIG. 11C, and the cross-section of the illuminance distribution at y=0 mm is depicted in FIG. 11D. From these two figures, it can be observed that the illuminance remains almost unchanged with the radius of the illumination pattern ranging from 0 mm to about 100 mm, which provides evidence of excellent irradiance uniformity over the field of view within the range of at least ±40°. Although the illuminance decreases a little bit with the radius of the pattern increasing from 100 mm to 125 mm, the overall quality of illumination in the region [0 mm, 125 mm] is still practically acceptable, as it meets the requirement that good illumination be achieved on the region [0°, 40°].

Figure 11E:
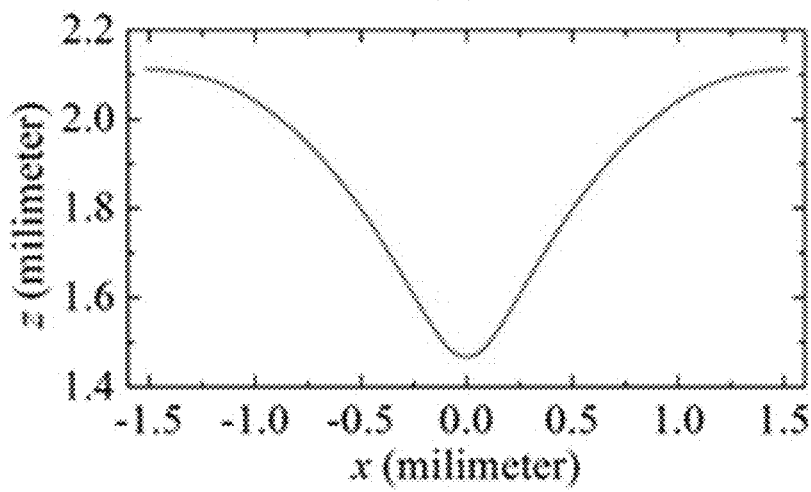

The 2D profile lens profile of an output surface 820 of an individual lenslet 430 (or, a cross section of an individual indentation in the surface 420 A) is depicted in FIG. 11E. Let H denote the z-coordinate 9 the coordinate along the optical axis) of the vertex of the lenslet. From FIG. 11E, we H=1.4673 mm. As a result, the ratio of the distance between the lenslet and the source to the size of the source (d=0.8 mm) is H/d=4.8341, demonstrating a very compact size of the individual lenslet.

TABLE 3

| Coefficients | comment | |
|---|---|---|
| $b_0$ | $\beta_0$ | 1 |
| $b_1$ | $\beta_2$ | 0.5350 |
| $b_2$ | $\beta_4$ | 0.8927 |

TABLE 4

| Coefficients | comment | |
|---|---|---|
| $c_0$ | $x^0$ | 1.46735047295568 |
| $c_1$ | $x^2$ | 3.00852805157124 |
| $c_2$ | $x^4$ | −16.0990608708102 |
| $c_3$ | $x^6$ | 71.679189140734 |
| $c_4$ | $x^8$ | −212.008388789171 |
| $c_5$ | $x^{10}$ | 392.887944657583 |
| $c_6$ | $x^{12}$ | −422.491580679514 |
| $c_7$ | $x^{14}$ | 180.840573495728 |
| $c_8$ | $x^{16}$ | 131.233894929999 |
| $c_9$ | $x^{18}$ | −229.458555133075 |
| $c_{10}$ | $x^{20}$ | 130.667667747074 |
| $c_{11}$ | $x^{22}$ | −34.6694015649846 |
| $c_{12}$ | $x^{24}$ | 10.7694235862715 |
| $c_{13}$ | $x^{26}$ | −8.75190384329995 |
| $c_{14}$ | $x^{28}$ | 2.59875250712619 |
| $c_{15}$ | $x^{30}$ | 0.731383332262212 |
| $c_{16}$ | $x^{32}$ | −0.147230689642778 |
| $c_{17}$ | $x^{34}$ | −0.40703974740316 |
| $c_{18}$ | $x^{36}$ | 0.237488418719023 |
| $c_{19}$ | $x^{38}$ | −0.0522663127715378 |
| $c_{20}$ | $x^{40}$ | 0.00426319995814002 |

Step 6: Formation of the Lens System (Array of Lenslets)

Figures 12A, 12B, 12C:
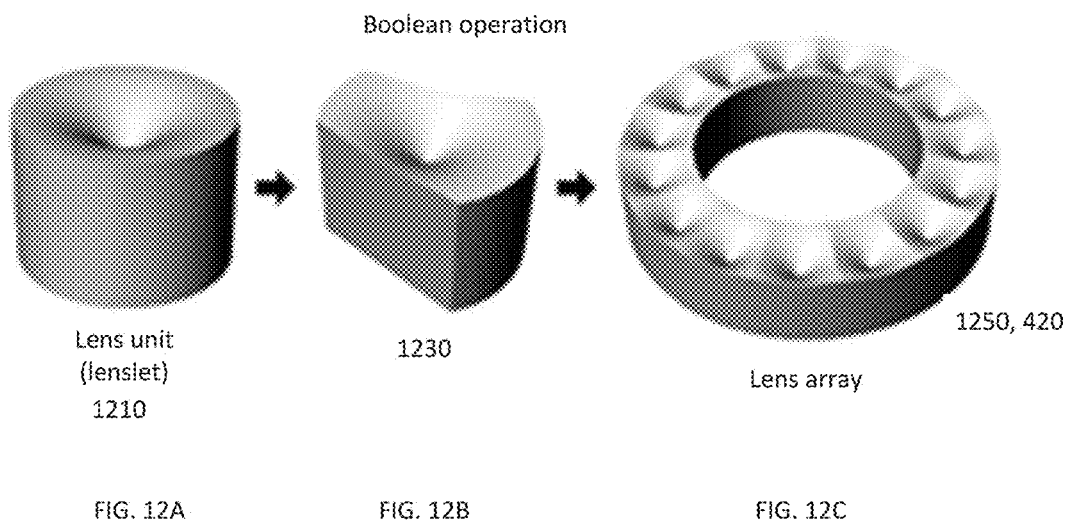
FIGS. 12A, 12B, and 12C schematically illustrate, in isometric views, examples of an individual lenslet (a lens unit), a trimmed version of such lens unit, and a lens system (configured as an array of aspherical lenslets), respectively.
Figure 13:
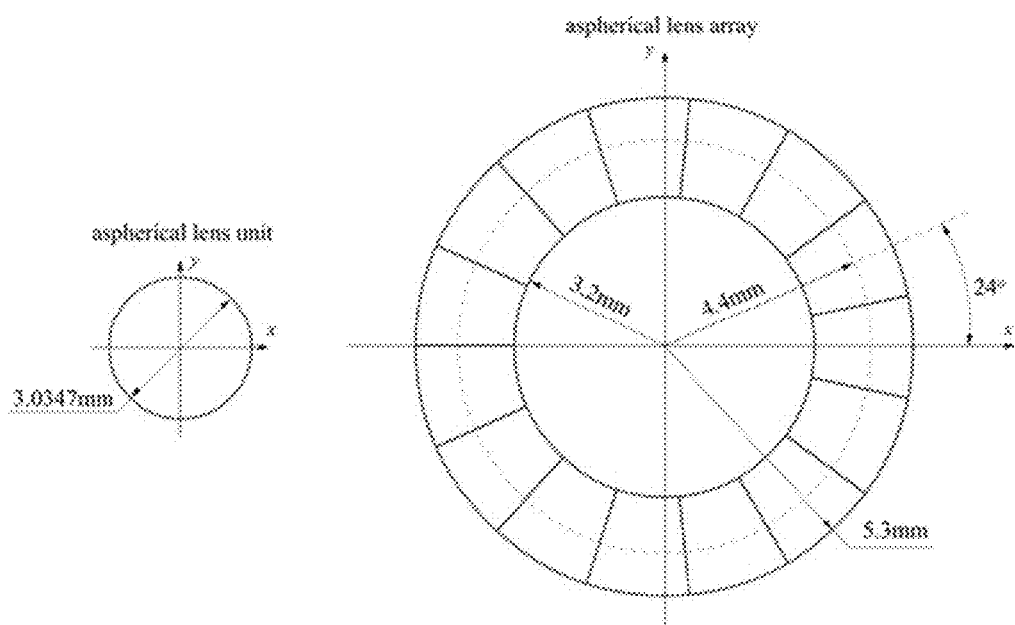
FIG. 13 is a schematic diagram illustrating an example of the lens system from individual (constituent) trimmed aspherical lenslets.

After obtaining the 2D profile of the individual lenslet, a rotationally-symmetric aspherical lens unit, as shown in FIG. 1wA, is obtained by rotating the lens profile about the optical axis of the system that is spatially separated from the optical axis of the individual lenslet. In one example, the diameter of the aspherical lenslet equals 3.0347 mm. It is then further transformed with a Boolean operation to trim the initial cylindrical shape of the lenslet 1210, to remove the extra lens material such that a multiplicity of so reshaped lenslets could form a ring, annularly-shaped optical plate when affixed adjacent to one another. The concept of so-reshaping the individual lenslet is shown in FIG. 12B, where the re-shaped lenslet is shown as 1230. The final aspherical lens array or lens system 420 is created by adjoining a plurality (e.g., 15) of the trimmed aspherical lenslets 1230 in an annulus about the optical axis of the laparoscope, as shown in FIG. 12C. In the aspherical lens array 1250, the distance between the center of the individual aspherical lenslet 1230 and the optical axis (the rotation axis) of the aspherical lens array 1250 equals 4.4 mm, and the rotation angle equals 24° (for the system 1250 that contains 15 individual lenslets 1230), as illustrated in FIG. 13, The inner and the outer radii of the aspherical lens array 1250 equaled 3.2 mm and 5.3 mm, respectively. The height of the lens array 1250 (the thickness of the annularly-shaped optical plate formed by the array 125) equaled 2.1052 mm.

Fabrication and Testing of an Embodiment

Figure 14A:
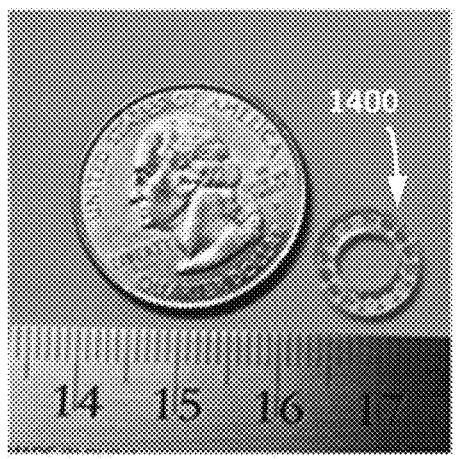
FIGS. 14A, 14B, 14C, 14D respectively illustrate a lens system fabricated in accordance with the embodiment of the present invention; the illumination pattern produced by the updated illumination system of a laparoscope (that is, by a conventional illumination system of a laparoscope, equipped with such lens system) on a specified screen; the normalized distribution of illuminance; and the normalized distribution of intensity produced by the updated illumination system.
Figure 14B:
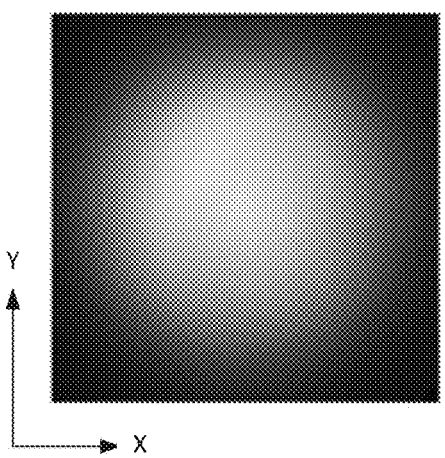
Figure 14C:
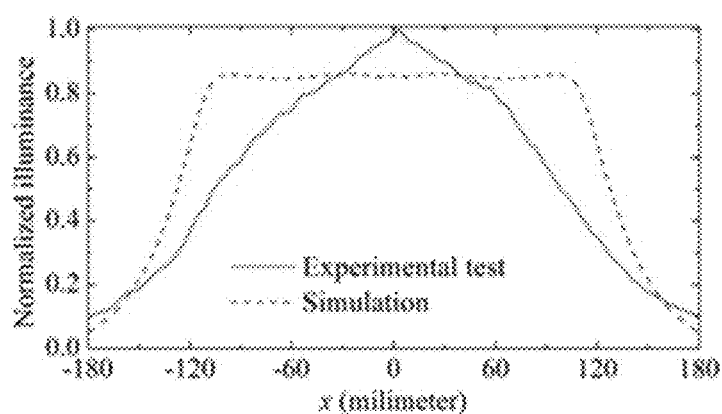
Figure 14D:
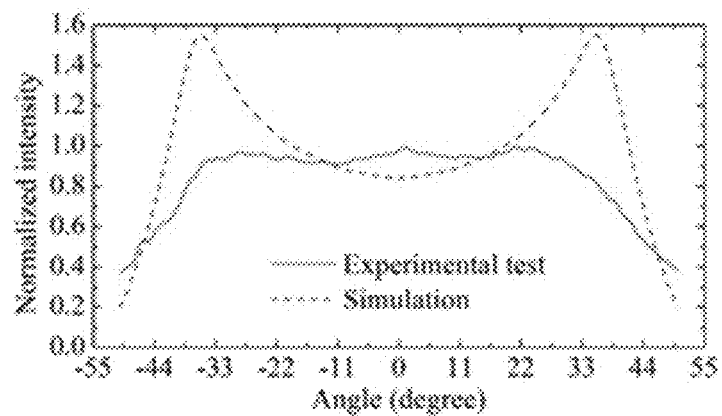

FIG. 14A shows a prototype of the lens system 1400 containing an array of aspheric, negative optical power lenslets fabricated with the turning diamond tool. The lens array 1400 along with an aperture array (configured according to 440) were attached to the distal end of the illumination system of laparoscope 1 of FIG. 1A to form a system structured as shown in FIG. 3A. FIG. 14B illustrates the illumination field produced by the so-configured illumination system of the laparoscope on an acrylic sheet at a lighting (working) distance of 150 mm. FIG. 14C presents plots illustrating the normalized distribution of illuminance determined along a line passing through the center of the pattern of FIG. 14B and parallel to the x-axis, while FIG. 12C is a plot showing the distribution of intensity determined along the same line. Some differences between the experimental and simulation results could be observed, that were attributed to (1) the underlying assumption that portions of the outgoing beam outcoupled through circular apertures in the screen have the same intensity distribution as the one shown in FIG. 6; (2) the errors associated with the machining (fabrication) of the lenslet array; and (3) the errors in alignment of the screen component with the lens system component. The RMS error for the illuminance distribution in the range of [−180 mm, 180 mm] was estimated to be 0.3011, while the RMS error for the intensity distribution in the range [−50.2°,50.2°] was estimated to be 0.3010.

Figure 15A:
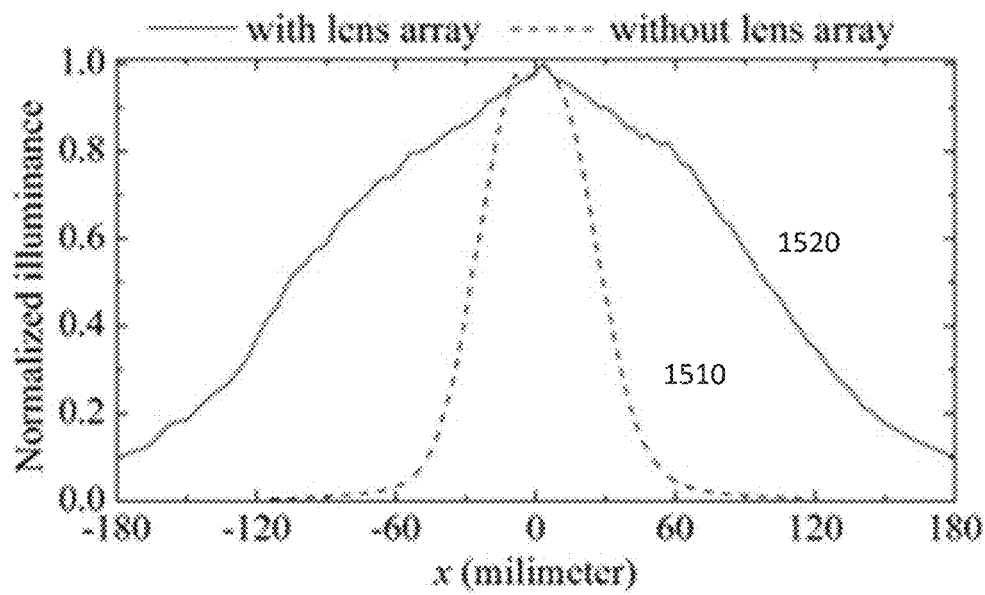
FIGS. 15A, 15B are plots illustrating comparison between the optical performance of a conventional laparoscope (without a lens array) and that of an embodiment of the invention (with lens array).
Figure 15B:
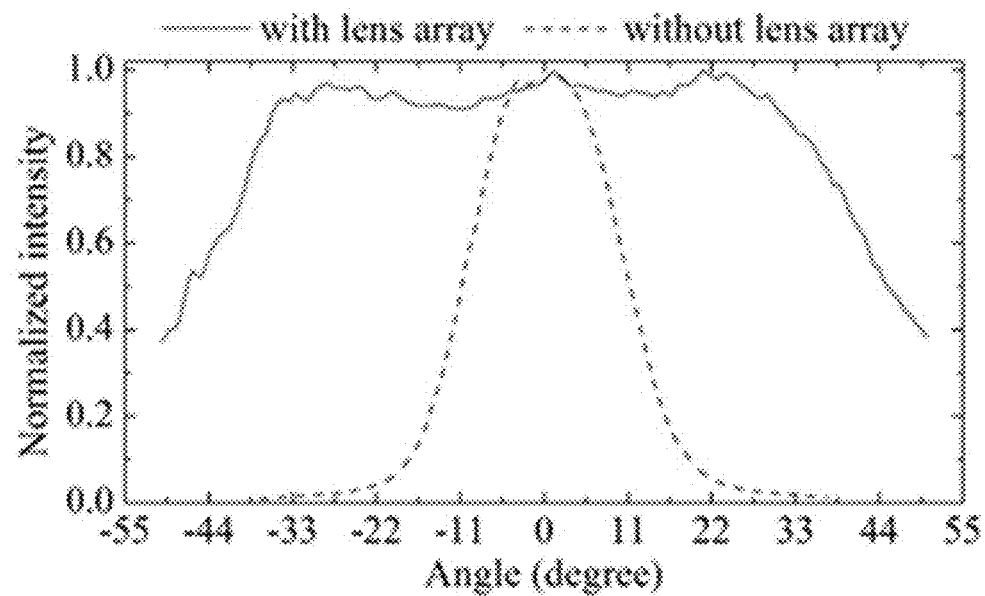

Additional empirical comparison was made between the distribution of the light output from the initial (not modified) illumination system of the laparoscope (that is, the light output outcoupled directly from the output end facet of the lightguide 204) and that of the transformed, integrated with the lens system. The results are illustrated in FIGS. 15A, 15B. Although the actual illuminance distribution deviates somewhat from the target, design, uniform distribution shown in FIG. 14C in the dashed line, it can nevertheless be asserted that the spatial distribution of radiant energy outcoupled is wider that that produced by a conventional laparoscope (that is, the FOV of the illumination system was visibly increased as a result of the proposed physical transformation of the illumination system). For example, comparison of the full-widths-at-half-maximum (FWHM) values provides the increase from about 30 (for the curve 1510) to about 100 (for the curve 1520). At the same time, the value of illuminance decreases at a lower rate from the center to the edge of the illumination pattern as compared to the rate observed with the use of the conventional laparoscope.

Figure 16A:
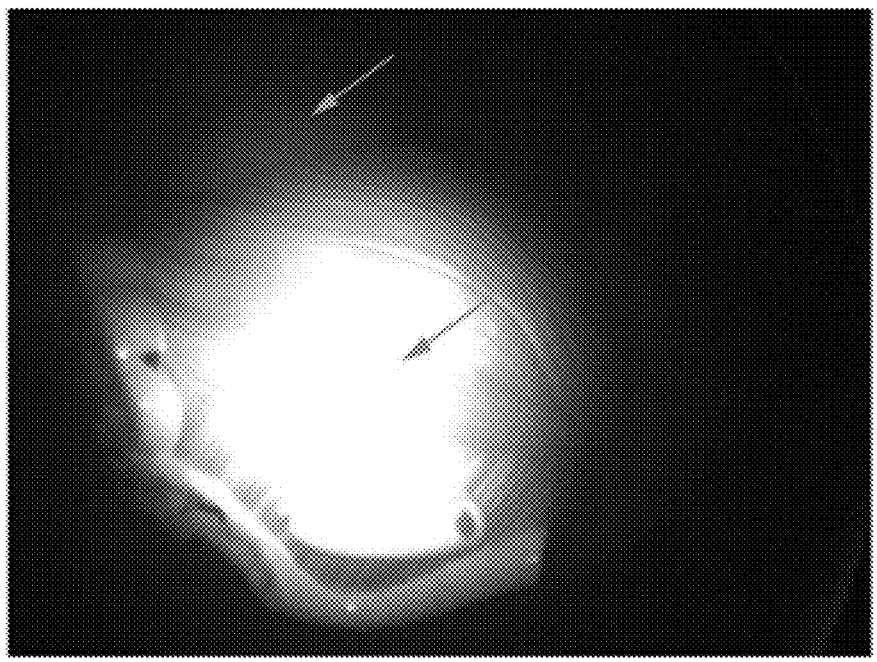
FIGS. 16A, 16B are images of an object illuminated with the use of a conventional laparoscope and with the use of an embodiment of the invention, respectively, under otherwise equal conditions.
Figure 16B:
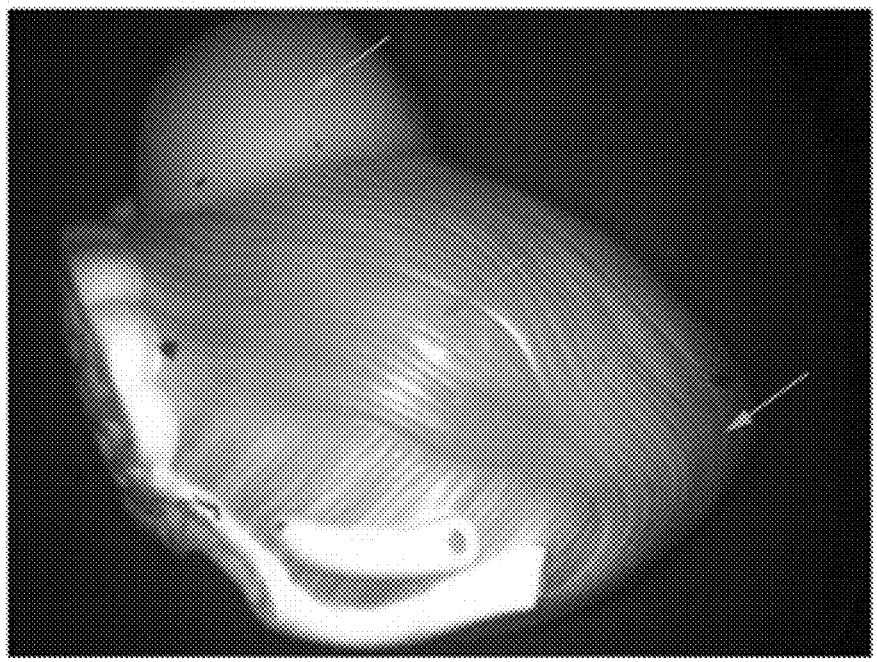
Figure 17:
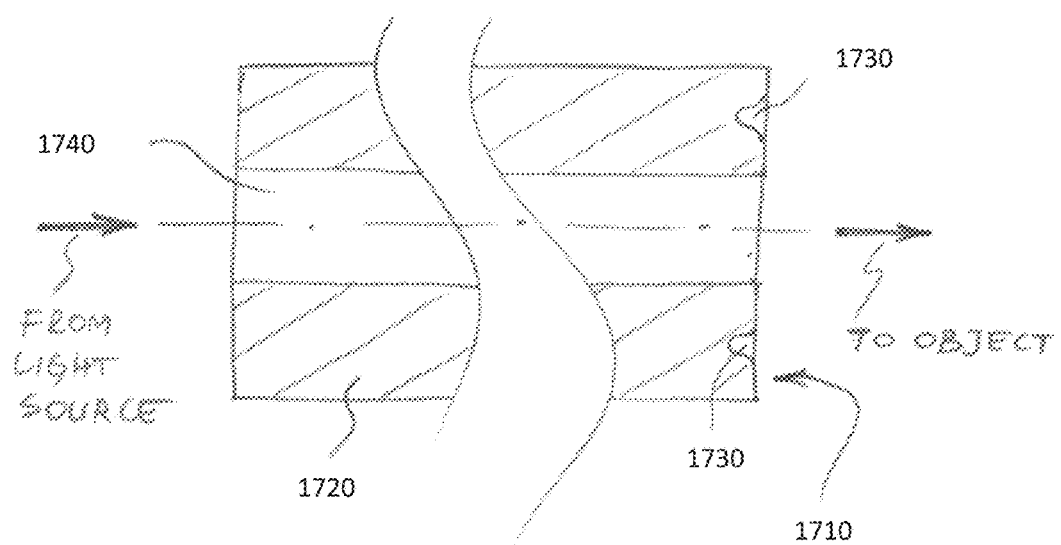
FIG. 17 shows schematically a related embodiment of the invention.

It is readily apparent, therefore, that the optical performance of the laparoscope transformed according to an embodiment of the invention is significantly improved. Images of the model target, captured when illuminated with the light output. FIG. 16A is a reiteration of FIG. 1E, illustrating the results of illumination of the chosen target with light outcoupled from the laparoscope having a conventional illumination system (that is, the illumination system the output end surface of which is substantially flat). Here, the majority of the target cannot be clearly observed either due to the over exposure (caused by the highly spatially concentrated light distribution in the center of the field) or due to very dim lighting near the edge of the field. FIG. 16B, on the other hand, demonstrated definite improvements in visibility of the structural details of the same target illuminated with light outcoupled from the transformed laparoscope, which has the illumination system containing the lens system 1400 of the invention.

It will be readily recognized by those skilled in the art that appropriate changes or modifications may be made to the above-described embodiments without departing from the broad inventive concepts of the invention. For example, in a related implementation of the embodiment of the invention, the output facet of the lightguide 204 can be molded or sculpted or milled or otherwise transformed from the one having a planar surface to the one having a surface with a plurality of indentations as was described in reference to FIGS. 3B, 4A such as to add a non-zero optical power to the previously powerless optical surface. As illustrated in FIG. 16, following the description of the component 420, 1400, the output surface 1610 of the lightguide 1620 is appropriately reshaped to contain an array of negative power lenslets (in one embodiment—aspheric lenslets) formed with the array of surface indentations 1630. Numeral 1640 identifies a hollow corresponding to the optics tube 212 of a laparoscope of FIG. 2, In reference to either of FIGS. 3A, 3B, 4A and 16, an illumination system configured for use with a laparoscope according to the invention, therefore, most generally includes an optical component made of an optically-transparent material and having a thickness defined between two surfaces each of which is transverse to the optical axis of the optical component, where a first surface of said two surfaces contains a plurality of indentations disposed along a closed curve that circumscribes the optical axis. Each of the indentations has a corresponding axis of symmetry that is perpendicular to the first surface, and a cylindrical portion of the optical component defined about an axis of symmetry of a given indentation forms an aspheric lenslet dimensioned to increase a degree of divergence of light incident onto the first surface through a second surface of the two surfaces. In one case, such cylindrical portion is a rotationally-symmetrical cylindrical portion. The optical component carries, therefore, a plurality of aspheric lenslets disposed adjacent to one another to form an annular array of aspheric lenslets. The optical component generally has an aperture therethrough, which aperture is symmetrical about the optical axis and devoid of the optically-transparent material.

A specific embodiment of the illumination system additionally contains a screen having an optically-opaque area. When the optical component defines a first projected area on a plane that is transverse to the optical axis, the screen is dimensioned to define a second projected area on the same plane, so the first and second projected areas are congruent with one another. The screen may be rotationally symmetric about the optical axis and include an optically-transparent aperture centered at the optical axis. Alternatively or in addition, the screen is formatted to contain a plurality of optically-transparent apertures, which are made to circumscribe the central optically-transparent aperture. When the illumination system is complemented with such screen, the screen is oriented to dispose each aperture from the plurality of optically-transparent apertures against and in spatial registration with a respective indentation from the plurality of indentations. In this case, the lightguide of the illumination system has its output end surface abutted directly against the screen such as to sandwich the screen between the optically-transparent component and the lightguide.

In one embodiment, a method of imaging a target with a laparoscope (that has an illumination system that contains a lightguide) includes transmitting light through the lightguide towards a distal end thereof; and outcoupling this light from the distal end through an end surface of an illumination system and a plurality of indentations in the end surface (the indentation from the plurality of indentations being disposed in an elliptical arrangement around an optical axis of the lightguide). A specific implementation of the method may further include a step of receiving light, transmitted through the lightguide and a planar output facet of the lightguide, at a lens system having (i) a first planar surface facing the output facet of the lightguide and (ii) a second surface that is the end surface of the illumination system. This specific implementation additionally includes the step of passing said light, transmitted through the lightguide and the planar output facet of the lightguide, through a plurality of apertures in an optically-opaque screen disposed between the planar output facet of the lightguide and the lens system. Alternatively or in addition, the embodiment of the method may further include transmitting light through the lens system that contains an annularly-shaped array of aspheric lenslets. The step of outcoupling may include outcoupling light, transmitted through the lightguide, through an output facet of the lightguide, where the output facet forms the end surface at the distal end of the illumination system.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes. In some specific cases, which are within the scope of the invention, the terms "approximately" and "about", when used in reference to a numerical value, represent a range of plus or minus 20% with respect to the specified value, more preferably plus or minus 10%, even more preferably plus or minus 5%, most preferably plus or minus 2% with respect to the specified value.

References made throughout this specification to "one embodiment," "an embodiment," "a related embodiment," or similar language mean that a particular feature, structure, or characteristic described in connection with the referred to "embodiment" is included in at least one embodiment of the present invention. Thus, appearances of these phrases and terms may, but do not necessarily, refer to the same implementation. It is to be understood that no portion of disclosure, taken on its own and in possible connection with a figure, is intended to provide a complete description of all features of the invention.

It is also to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed.

The invention as recited in claims appended to this disclosure is intended to be assessed in light of the disclosure as a whole, including features disclosed in prior art to which reference is made.

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

What is claimed is:

1. An article of manufacture comprising:
an optically-transparent component having an optical axis and a thickness defined between first and second surfaces each of which is transverse to the optical axis,
wherein said optically-transparent component defines a first projected area on a plane that is transverse to the optical axis,
wherein one of the first and second surfaces contains a plurality of indentations disposed along a closed curve that circumscribes the optical axis; and
a screen having an optically-opaque area, the screen dimensioned to define a second projected area on said plane, the first and second projected areas being congruent with one another.

2. An article of manufacture according to claim 1, wherein said closed curve is an ellipse.

3. An article of manufacture according to claim 1, wherein said one of the first and second surfaces contains a surface area with a cross-sectional profile represented by an even polynomial function $z = \Sigma_{m=0}^{20} C_m x^{2m}$,
wherein x is a coordinate measured along said one of the first and second surfaces and $C_m$ represents a polynomial coefficient.

4. An article of manufacture according to claim 1, wherein said optically-transparent component includes a plate.

5. An article of manufacture according to claim 4, wherein said plate has a cross-section with a perimeter defined by a differentiable closed curve, said cross-section defined in a plane that is transverse to the optical axis.

6. An article of manufacture according to claim 4, wherein said plate has a planar surface.

7. An article of manufacture according to claim 4, wherein said plate has an annularly-shaped cross section in a plane that is transverse to said optical axis.

8. An article of manufacture according to claim 1, wherein said screen has a plurality of optically-transparent apertures therein.

9. An article of manufacture according to claim 1, further comprising a lightguide in optical communication with the optically-transparent component through said screen.

10. An article of manufacture according to claim 1, further comprising a lightguide with an end surface that is abutted directly against said optically-transparent component.

11. An article of manufacture according to claim 1, wherein said optically-transparent component includes a lightguide having a length that is equal to said thickness.

12. An article of manufacture according to claim 11, wherein said light-guide includes a flexible bundle of optical fibers.

13. An endoscope comprising an article of manufacture according to claim 1.

* * * * *

UNITED STATES PATENT AND TRADEMARK OFFICE
CERTIFICATE OF CORRECTION

PATENT NO. : 10,481,386 B2
APPLICATION NO. : 15/471994
DATED : November 19, 2019
INVENTOR(S) : Hong Hua, Rengmao Wu and Yi Qin It is certified that error appears in the above-identified patent and that said Letters Patent is hereby corrected as shown below:

In the Claims

Column 18, Claim 3, Line 4:
"profile represented by an even polynomial function $Z=\sum_{m=0}^{20} C_m x^{2m}$"

Should read:

-- profile represented by an even polynomial function $z = \sum_{m=0}^{20} C_m x^{2m}$ --

Signed and Sealed this
Twenty-first Day of January, 2020

Andrei Iancu
*Director of the United States Patent and Trademark Office*